(12) United States Patent
Agmon

(10) Patent No.: US 8,444,566 B2
(45) Date of Patent: May 21, 2013

(54) GUIDE FOR PLACEMENT OF CATHETER INTO BRAIN AND A METHOD OF UTILIZING THE SAME

(76) Inventor: Arnon Agmon, Tel Aviv (IL)

(*) Notice: Subject to any disclaimer, the term of this patent is extended or adjusted under 35 U.S.C. 154(b) by 1190 days.

(21) Appl. No.: 12/120,247

(22) Filed: May 14, 2008

(65) Prior Publication Data

US 2008/0287916 A1    Nov. 20, 2008

Related U.S. Application Data

(60) Provisional application No. 60/917,683, filed on May 14, 2007.

(51) Int. Cl.
*A61B 8/14* (2006.01)

(52) U.S. Cl.
USPC .......................................... 600/459; 600/437

(58) Field of Classification Search
USPC ................................. 600/437–469
See application file for complete search history.

(56) References Cited

U.S. PATENT DOCUMENTS

| | | | |
|---|---|---|---|
| 4,497,325 A * | 2/1985 | Wedel | 600/567 |
| 4,613,324 A | 9/1986 | Ghajar | |
| 4,681,103 A * | 7/1987 | Boner et al. | 606/1 |
| 4,742,829 A * | 5/1988 | Law et al. | 600/461 |
| 4,877,033 A * | 10/1989 | Seitz, Jr. | 600/441 |
| 4,883,059 A * | 11/1989 | Stedman et al. | 600/437 |
| 5,280,427 A * | 1/1994 | Magnusson et al. | 600/407 |
| 6,210,330 B1 * | 4/2001 | Tepper | 600/439 |
| 6,267,770 B1 * | 7/2001 | Truwit | 606/130 |
| 2003/0233046 A1 * | 12/2003 | Ferguson et al. | 600/437 |
| 2009/0118612 A1 * | 5/2009 | Grunwald et al. | 600/424 |

FOREIGN PATENT DOCUMENTS

| WO | WO/2006/062668 | 6/2006 |
|---|---|---|
| WO | WO/2006/093206 | 9/2006 |
| WO | WO/2007/001001 | 1/2007 |

* cited by examiner

*Primary Examiner* — Sanjay Cattungal

(57) ABSTRACT

The subject matter discloses a method and apparatus for detecting an environment within a body comprising a stylet and a catheter capable of being inserted into the body and a bio-sensing module for detecting a predefined material within the body, upon insertion of the stylet and catheter with close proximity to the predefined material. The predefined material may be beta-transferrin, and the apparatus may comprise a transmitter and an indication unit for transmitting data related to the presence of the predefined material in the body.

4 Claims, 9 Drawing Sheets

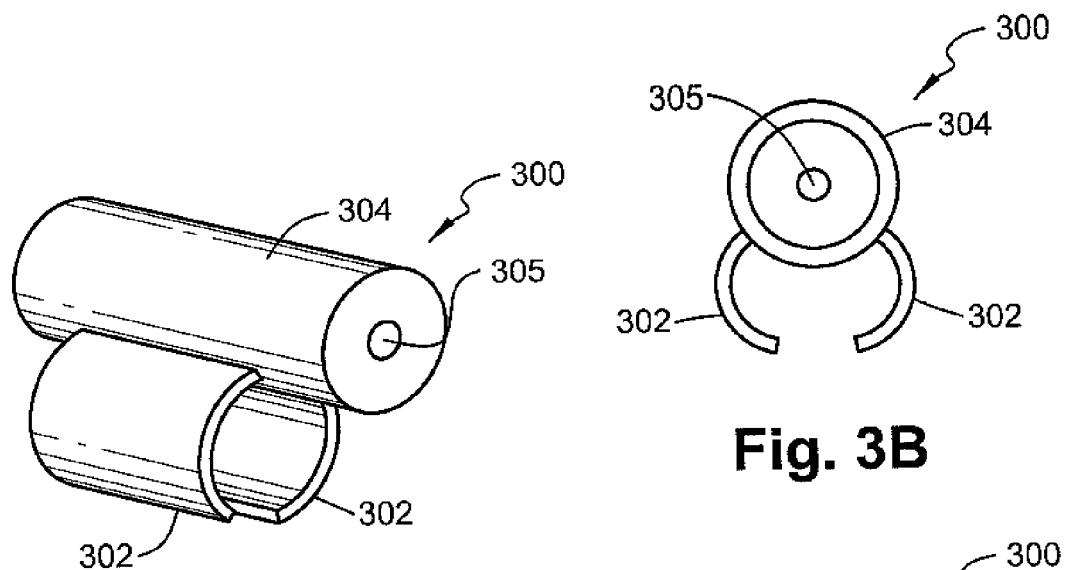
Fig. 3B
Fig. 3A
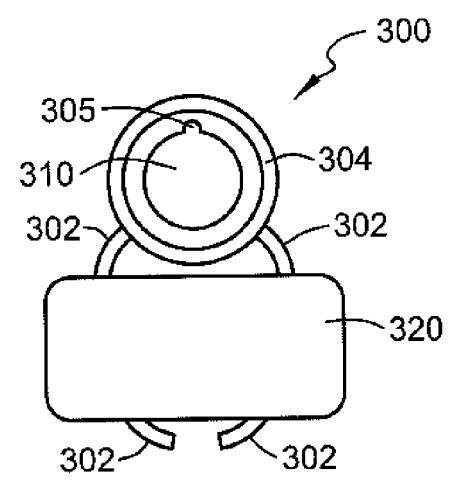
Fig. 3C
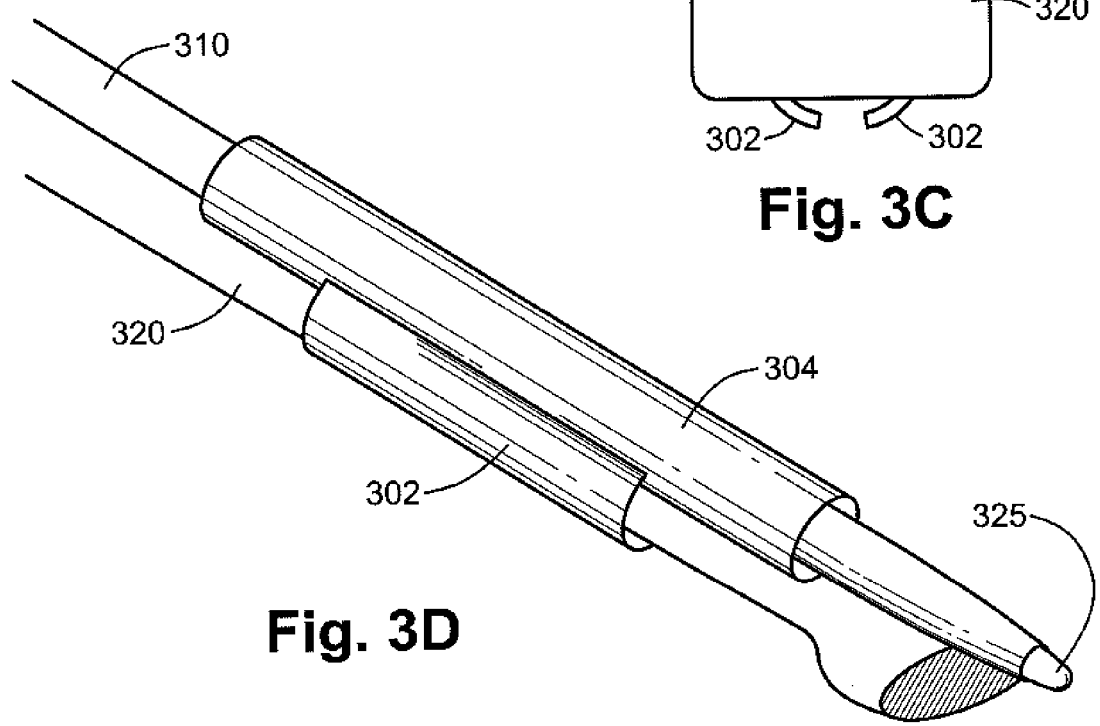
Fig. 3D

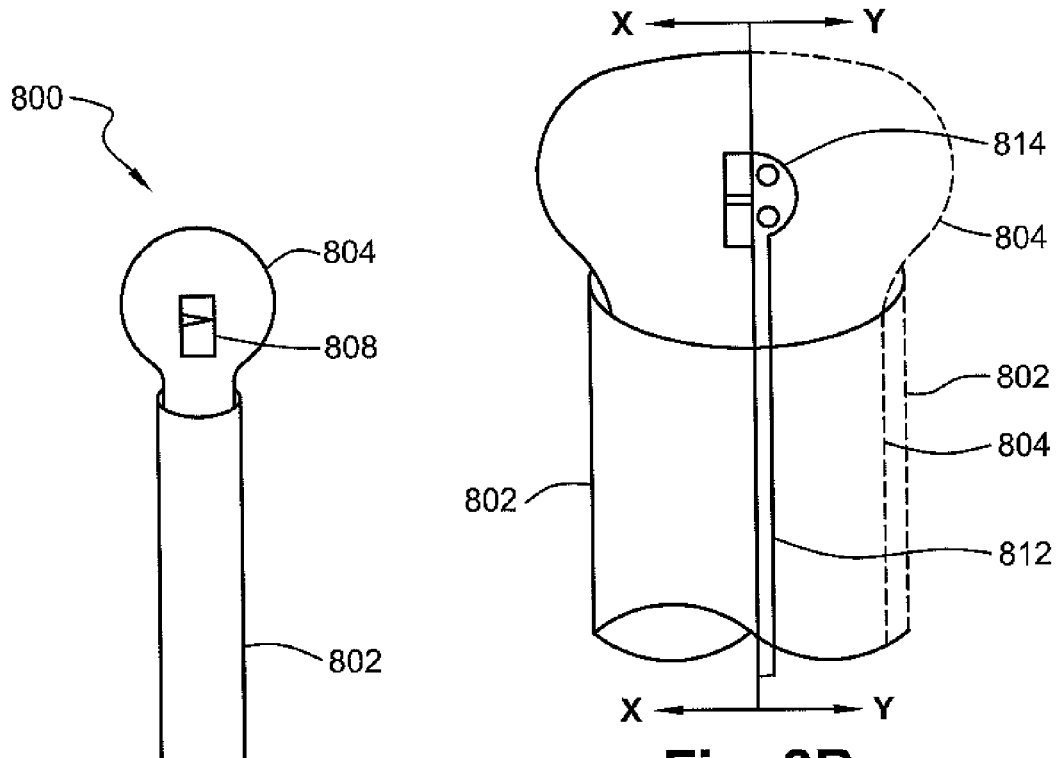
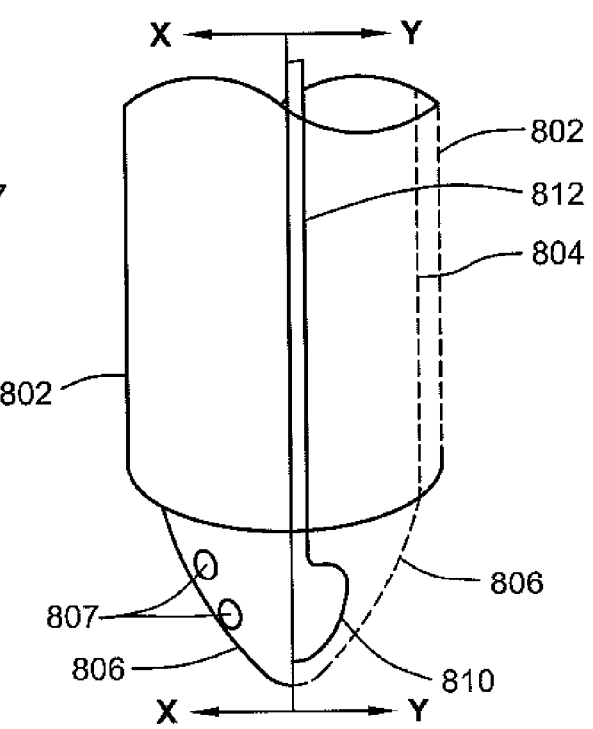
Fig. 8A
Fig. 8B
Fig. 8C

GUIDE FOR PLACEMENT OF CATHETER INTO BRAIN AND A METHOD OF UTILIZING THE SAME

FIELD OF THE INVENTION

The present invention relates to a catheter guiding apparatus and methods for accurately inserting or placing a catheter into a body organ, such as a chamber inside the brain.

BACKGROUND OF THE INVENTION

In the central nervous system, the brain and spinal cord are surrounded by a clear and colorless fluid termed cerebrospinal fluid (CSF). In addition, the CSF fills inside brain chambers called ventricles. Normally, CSF is produced by intra ventricular organelles, the choroids plexus, and flows through the ventricles and exits the brain through several foramina where its bathes the surfaces of the brain and spinal cord and finally absorbed into the bloodstream. The balance between production and absorption of CSF is critically important. Ideally, the fluid is almost completely absorbed into the bloodstream as it circulates; however, there are circumstances which, when present, will prevent or disturb the production or absorption of CSF, or which will inhibit its normal flow. When this balance is disturbed, hydrocephalus will result. Hydrocephalus is characterized by an abnormal dilation of the brain ventricles. This dilation can cause potentially harmful pressure on the tissues of the brain and can cause a wide variety of symptoms such as headache and may lead to death. To overcome the deleterious effect of the excess of CSF a divergence of fluids from the brain ventricle via a ventricular shunt is required.

The etiology for hydrocephalus may be congenital or acquired. Congenital hydrocephalus can result from genetic inheritance (aqueductal stenosis) or developmental disorders such as those associated with neural tube defects including spina bifida and encephalocele. Other acquired causes include, intraventricular hemorrhage (one of the complications of premature birth), infections, tumors, traumatic head injury and intra cranial bleeding. In addition, many people develop hydrocephalus even when none of these factors are present.

Hydrocephalus is most often treated with the surgical placement of a shunt system. A ventricular shunt-tube is placed to drain fluid from the ventricular system in the brain to an external reservoir (ventriculostomy) or to a cavity in the body, for instance a cavity of the abdomen (ventriculo-peritoneal shunt). The tubing may contain a valve to ensure the direction, flow or the pressure of the fluid being diverge.

Prior to a ventricular shunt procedure, diagnostic techniques, such as computed tomography scan (CT scan) or magnetic resonance imaging (MRI), are performed to confirm the diagnosis and for the purpose of planning the neurosurgical procedure. In the surgical procedure a ventricular catheter is inserted with the aim to be placed in the body of the ventricle usually, lateral ventricle. The ventricular catheter insertion point and trajectory rely on surface anatomy landmarks, on the preformed imaging data and the surgeon's sense of spatial orientation. However, such techniques are not accurate and may lead to mat-position of said catheter which may cause complications such as bleeding, damage to fundamental brain structure and the like. Misplacement of said catheter usually entails further diagnostic procedures such as CT and MRI as well as additional surgical manipulation with the purpose of re-adjusting catheter location.

Various imaging technologies and methods have been used for computing a trajectory for catheter insertion. For instance, a neuronavigation system provides a real-time trajectory for accurate insertion or placement of a ventricular shunt catheter. However, in many cases it is not used due to cost considerations or due to the long setup time required relative to the time of the ventricular shunt procedure. In some cases such setup time takes more than 45 minutes, and requires fixation of the patient head.

A drawback of prior art systems is the inability to provide accurate placement in a short time or low cost without a significant amount of setup time relatively to the surgical procedure itself. Therefore, there is the need for an apparatus and methods for fast, cheap and accurate placement of a catheter or shunt into brain ventricles. Such method and apparatus will reduce morbidity and mortality while enhance time needed for the procedure at lower costs.

SUMMARY OF THE INVENTION

It is one object of the subject matter to disclose an apparatus for detecting an environment within a body comprising: an apparatus comprising a stylet and a catheter capable of being inserted into the body; a bio-sensing module for detecting a predefined material within the body, upon insertion of the stylet and catheter with close proximity to the predefined material.

In some embodiments, the bio-sensing module further indicates the presence of the predefined material. In some embodiments, the indication is provided using electrical connecting element.

In some embodiments, the predefined material is beta-transferrin. In some embodiments, the at least a portion of the bio-sensing module is located within the stylet. In some embodiments, the bio-sensing module comprises a biosensor, transmitter and an indication unit. In some embodiments, the bio-sensing module is located in a cavity within the stylet.

In some embodiments, the stylet further comprises one or more apertures for allowing fluid containing the predefined material to enter the stylet cavity. In some embodiments, the predefined material contacts and activates the bio-sensing module. In some embodiments, at least a portion of the biosensor is located outside surface of the stylet. It is one object of the subject matter to disclose a method of inserting a catheter or trocar into a body comprising: inserting an apparatus comprising a stylet and catheter into the body; detecting a predefined material by a biosensor connected to the apparatus upon close proximity of the apparatus to the predefined material.

In some embodiments, the method comprises a step of transmitting data related to the detection of the predefined material. In some embodiments, the further comprises a step of activating the biosensor by contact between the biosensor and the predefined material. In some embodiments, the forcing the biosensor to send electrical current through electrical connecting means to an indicator unit.

The present invention discloses an apparatus and method for accurately guiding a catheter into a chamber in the human or animal brain or into normal or abnormal brain tissue.

One non-limiting objective of the present invention is to provide accurate placement of a catheter into a chamber in the human or animal organ such as the brain, or into other parts of the organ or brain tissue, in a short time relative to the surgical procedure itself or to related procedures associated with the surgical procedure.

One other non-limiting object of the present invention is to provide accurate placement of a catheter into a chamber in the human or animal organ such as the brain or into other parts of the organ or brain tissue, at relative low cost relative to the surgical procedure itself or to related procedures associated with the surgical procedure.

One other non-limiting object of the present invention is to provide accurate placement of a catheter into a chamber in the human or animal brain or into other parts of the brain tissue, having a short setup time relative to the surgical procedure itself, or to related procedures associated with the surgical procedure.

There is thus provided in accordance with an exemplary embodiment of the invention an ultrasound probe adapted for guiding the placement of a catheter, comprising an ultrasound imaging probe; a catheter apparatus; and a catheter guiding and link apparatus guiding the catheter and joining the ultrasound probe and the catheter guiding apparatus.

There is thus provided a method of the present invention for the insertion of a specialized catheter into a brain ventricle or brain tissue using an ultrasound device coupled to the catheter.

The subject matter discloses an ultrasound probe adapted for guiding the placement of a catheter, comprising: an ultrasound imaging probe; a catheter guiding apparatus; and, a guiding-connector joining the ultrasound probe and the guiding apparatus.

The subject matter further discloses the ultrasound probe, wherein the guiding-catheter further comprising an at least one ultrasound probe holder or an at least one catheter holding member.

The subject matter discloses an ultrasound probe adapted for guiding the placement of a catheter, comprising: an ultrasound imaging probe; a catheter guiding apparatus mounted on said probe, the guiding apparatus comprising a tubular apparatus and a device for mounting the guiding apparatus on said probe.

The subject matter discloses a catheter guiding apparatus comprising a guiding-connector wherein the tubular apparatus having a curved cross-sectional area of a pre-determined diameter; and having an opening of certain dimensions.

The subject matter further discloses the connector of the guiding apparatus can be mounted on an ultrasound probe. The opening of the connector allows a catheter or trocar to move through it.

The subject matter further discloses the guiding-connector is made of a rigid or semi-rigid plastic, and can be serialized.

The subject matter further discloses the connector of the guiding apparatus includes a ring trip, the ring clip includes a pair of bendable arms to allow the apparatus to be mounted on an ultrasound probe.

A catheter delivery system comprising:
a. an ultrasound imaging probe;
b. a catheter guiding apparatus mounted on said probe comprising a guiding-connector;
c. a catheter or trocar that can be moved inside said guiding-connector.

The subject matter further discloses a method of accurately inserting a catheter or trocar, the method comprising: mounting a catheter guiding apparatus on an ultrasound probe; inserting a catheter or a trocar through the mounted guiding apparatus; determining a trajectory using the ultrasound imaging probe; and, inserting the catheter or a trocar through the mounted guiding apparatus, using the trajectory found.

BRIEF DESCRIPTION OF THE FIGURES

Non-limiting embodiments of the invention will be described with reference to the following description of exemplary embodiments, in conjunction with the figures. The figures are generally not shown to scale and any sizes are only meant to be exemplary and not necessarily limiting. In the figures, identical structures, elements or parts that appear in more than one figure are preferably labeled with a same or similar number in all the figures in which they appear, in which:

FIGS. 3A-3D shows one embodiment of the present invention, in accordance with exemplary embodiments of the subject matter;

DETAILED DESCRIPTION OF EXEMPLARY EMBODIMENTS

Figure 1:
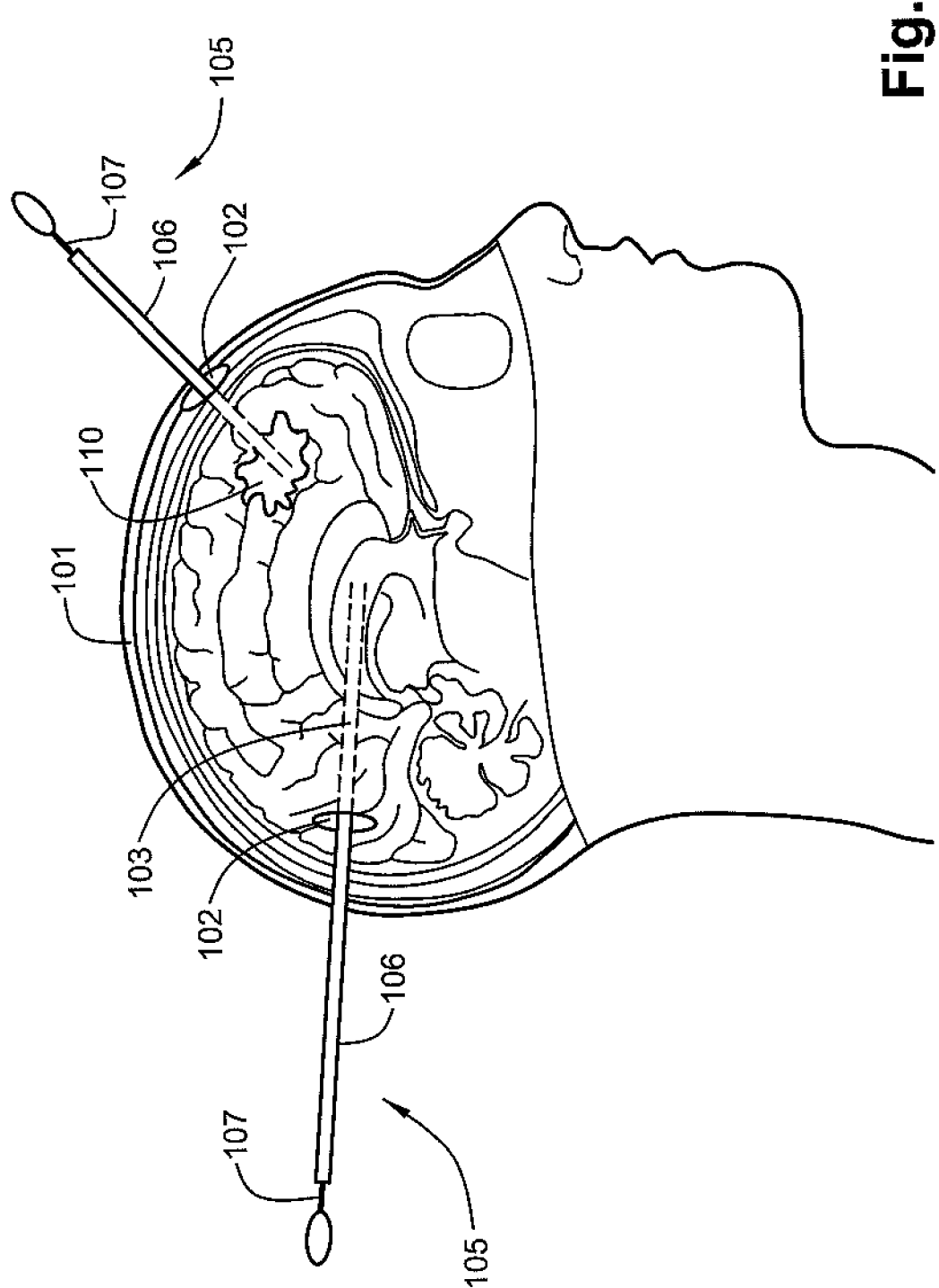
FIG. 1 is a side view of the human head with brain ventricles position and contour highlighted through skull illustrating several locations for insertion of a ventricular catheter in the body of the lateral ventricle of the human brain together with an exemplary positioning of catheter into brain space occupying lesion, in accordance with one preferred embodiment disclosed in the prior art.

FIG. 1 shows a patient's head 100 graphically represented with lateral ventricle 103 see-through or space occupying lesion (SOL) 110 see-through. A catheter 105 inserted into the brain lateral ventricle 103 and SOL 110 is shown. Typically, during such operation a hole or aperture 102 is drilled through a human skull 101 of a patient head 100. The location of said aperture 102 is determined according to anatomical landmarks. The catheter 105 typically is composed of a tube 106 and a stylet 107. In a prior art typical operation of said catheter, following the drilling of aperture 102 in skull 101 of the patients head 100, the operator aimed the catheter 105 towards the lateral ventricle 103 or SOL 110. Subsequently the catheter 105 is inserted through brain tissue (not shown) until fluid is accepted at one end of said catheter 105. This implies to the surgeon (not illustrated) that the catheter 105 is in proper position. At this point, stylet 107 is withdrawn and tube 106 is affixed to the patient's head 100. This allows the drainage of the lateral ventricle 103 which typically contains fluid to be drained. When catheter 105 is inserted into SOL 110 or other areas of the brain, the exact location of catheter 105 to be inserted is based upon previously prepared CT or MRI images as well as the use of Neuro-navigation system. Post insertion CT or MRI is typically performed as well.

Figure 2:
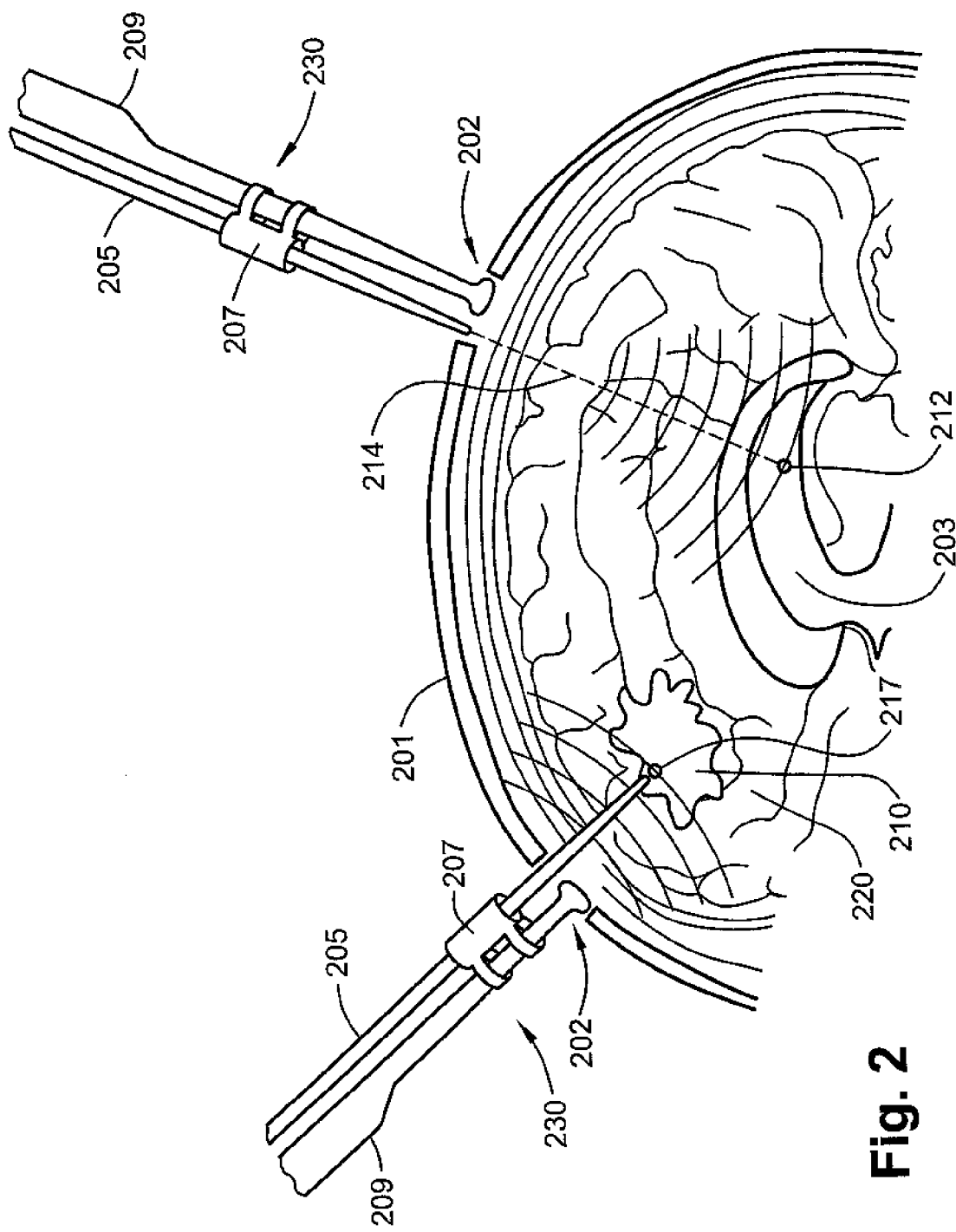
FIG. 2 is a schematic representation of the present invention during pre and post insertion, in accordance with one preferred embodiment disclosed in the subject matter.

FIG. 2 is a schematic presentation of the present invention in the pre and post insertion state where patient's head 200 is semi transparent, showing the brain 220 having lateral ventricle 203, space occupying lesion (SOL) 210 skull 201 and skull apertures (mechanical) 202. FIG. 2 also depicts catheter 205, Ultrasound probe (USp) 209 and guiding-connector apparatus 207. USp-Catheter guiding complex 230 is composed of catheter 205, USp 209 and Guiding-connector apparatus 207. USp-Catheter guiding complex 230 is typically assembled prior to insertion of catheter 205 into brain 220.

Complex 230 is shown on the right hand side of FIG. 2 prior to catheter 205 insertion into lateral ventricle 203. Following drilling of skull aperture 202, complex 230 is brought into contact with the Dura (not shown). Catheter target 212 is identified and trajectory 214 for the correct insertion of catheter 205 is determined Using USp 209. Following determination of catheter target 212 and correct trajectory 214, complex 230 may be fixed with a special fixation (not shown) such that catheter target 212 and trajectory 214 will not be lost.

On the left hand side of FIG. 2 there is depicted complex 230 where catheter 205 is already positioned in desired intra paranchymal brain location 217.

FIGS. 3A-3D are a schematic representation of the present invention and are provided together for a more complete description and understanding of the guiding catheter as well as methods of utilizing the guiding catheter. FIG. 3A is a schematic oblique view of the guiding-connector apparatus 300 of the present invention while FIG. 3B is a basic cross section view of the guiding-connector apparatus 300 of the present invention. FIG. 3C is an anterior-posterior view of the present invention where catheter 310 and probe such as US probe 320 are also illustrated in conjunction with the guiding-connector apparatus 300 of the present invention. FIG. 3D is an oblique view of the guiding-connector apparatus 300 of the present invention holding a ventricular catheter 310 and a probe 320 such as for example an ultrasound probe. The following description relates to FIGS. 3A, 3B, 3C, 3D. The apparatus of the present invention is a guiding-connector apparatus 300 constructed of catheter holding member 304 having aperture 305 and an Ultrasound probe holders 302. Member 304 and holders 302 are typically joined and are a part of guiding-connector apparatus 300. Guiding-connector apparatus 300 can be constructed such that member 304 and holders 302 are a part of one integral unit made of for example a polymer cast, metal cast or other rigid or semi rigid materials including any materials approved to use in a surgical environment. In another embodiment of the present invention, member 304 and holders 302 can be two different units joined. Joining member 304 and holders 302 can be achieved by any attaching elements or materials in the art such as, for example, glue, rivets, connectors, Velcro like members, iron wires, stapling elements and the like. The guiding-connector apparatus 300 of the present invention composed of member 304 and holders 302 is. depicted here as a single unit. Member 304 is preferably a hollow member, having aperture 305 and is typically substantially cylindrical or partially cylindrical shaped, specifically design to accommodate catheter 310 such that a smooth operation of said catheter 310 can be performed. Typically, catheter 310 is inserted through aperture 305 and driven through member 304. Holders 302 are designed to stably and firmly attach to the probe 320 such as ultrasound probe 320. Holders 302 displayed in the present embodiment of the present invention is a partially opened semi circular or partially polygonal member preferably using tensile force specifically designed to attach to said probe 320. Holders 302 can be adjustable to fit probe 320 via tensile force of its fabrication such that said probe 320 will be firmly attached to said holders 302. This can also be achieved via attaching elements present in the art such as glue, rivets, connectors, Velcro like members, iron wires, stapling elements, pins and the like. In the operation of the apparatus of the present invention the catheter 310 is inserted through member 304 via aperture 305 while at the same time holder 302 is fitted with probe 320 such that catheter 310 and probe 320 are at close proximity. A typical skull aperture (such as 102 of FIG. 1 and 202 of FIG. 2) is made to accommodate guiding-connector apparatus 300 holding both catheter 310 and probe 320. Guiding-connector apparatus 300 can be constructed such that two or more holders 302 are present in such a manner as to increase the holding strength of holders 302 onto Ultrasound probe 320.

It should be clear to the person skilled in the art that other embodiments used to hold the catheter 310 and probe 320 for the accurate placement of said catheter 310 into a brain tissue are within the scope of the present invention. Such embodiments may include specific members that snugly accommodate different sized catheters as well as different holders to hold different ultrasound probes.

Figure 4:
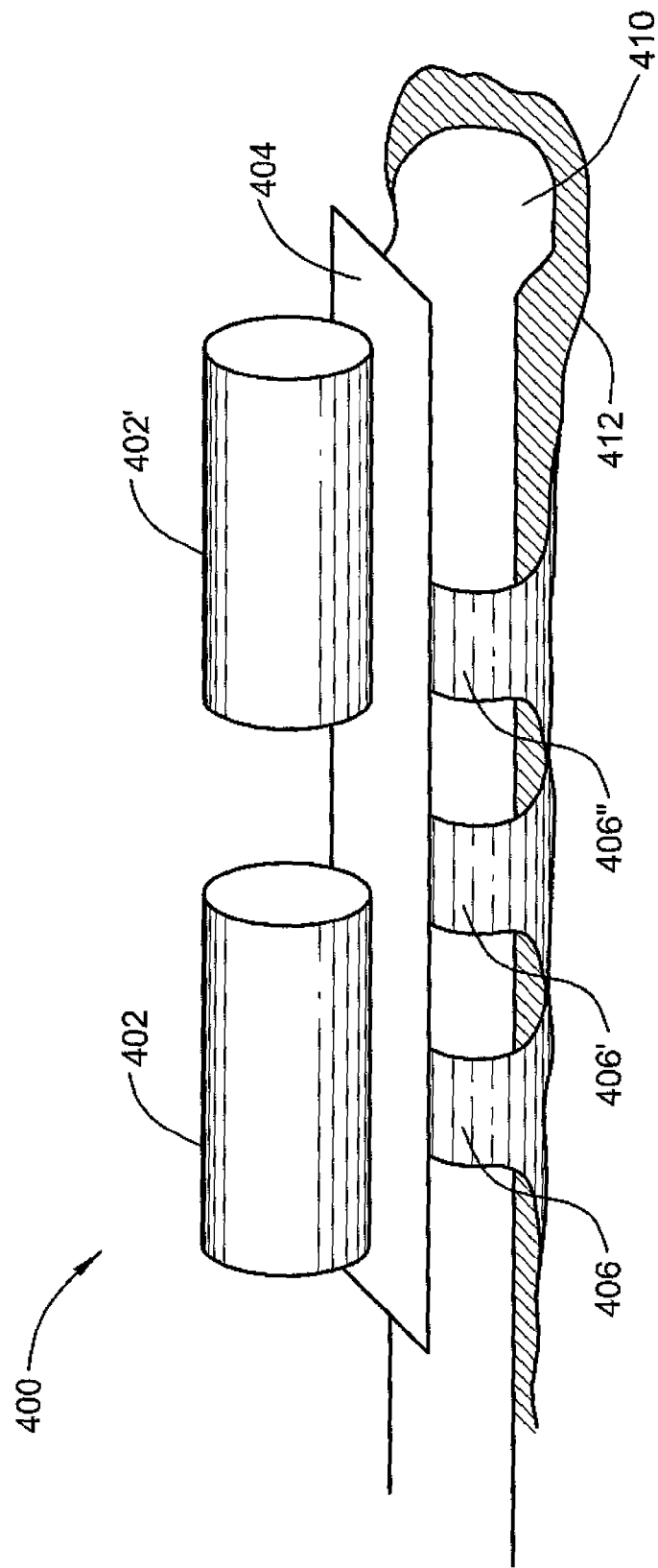
FIGS. 4, 5A and 5B show other exemplary embodiments of the subject matter.

In FIG. 4, another embodiment of the present invention is illustrated where guiding-connector apparatus 400 comprises one or more catheter holding members 402, 402" interconnected to plate 404 which has fastening elements 406, 406', 406". Guiding-connector apparatus 400 is illustrated holding an ultrasound probe 410 covered with condom 412 via fastening element 406. Said fastening element 406 can be constructed from tensile plastic material, tensile metal, Velcro attaching elements, and lock-in attaching band having two inter locking rails as well as other attaching elements known in the art. Said attachment can be permanent through the user of elements such as via rivets, or knits. According to specific Ultrasound probe 410 to be used, fastening elements 406, 406', 406" can be produced of varying sizes and shapes. Plate 404 can be a plastic or metal plate affixing catheter holding members 402, 402' as well as fastening elements 406, 406', 406". Catheter holding members are typically hollow having an aperture specifically suited to convey snugly catheter 205 (of FIG. 2). According to specific catheter to be used, catheter holding members can be produced of varying sizes and shapes. Said guiding-connector apparatus 400 can also be produced from a plastic or metal mold as one member.

Figure 5A:
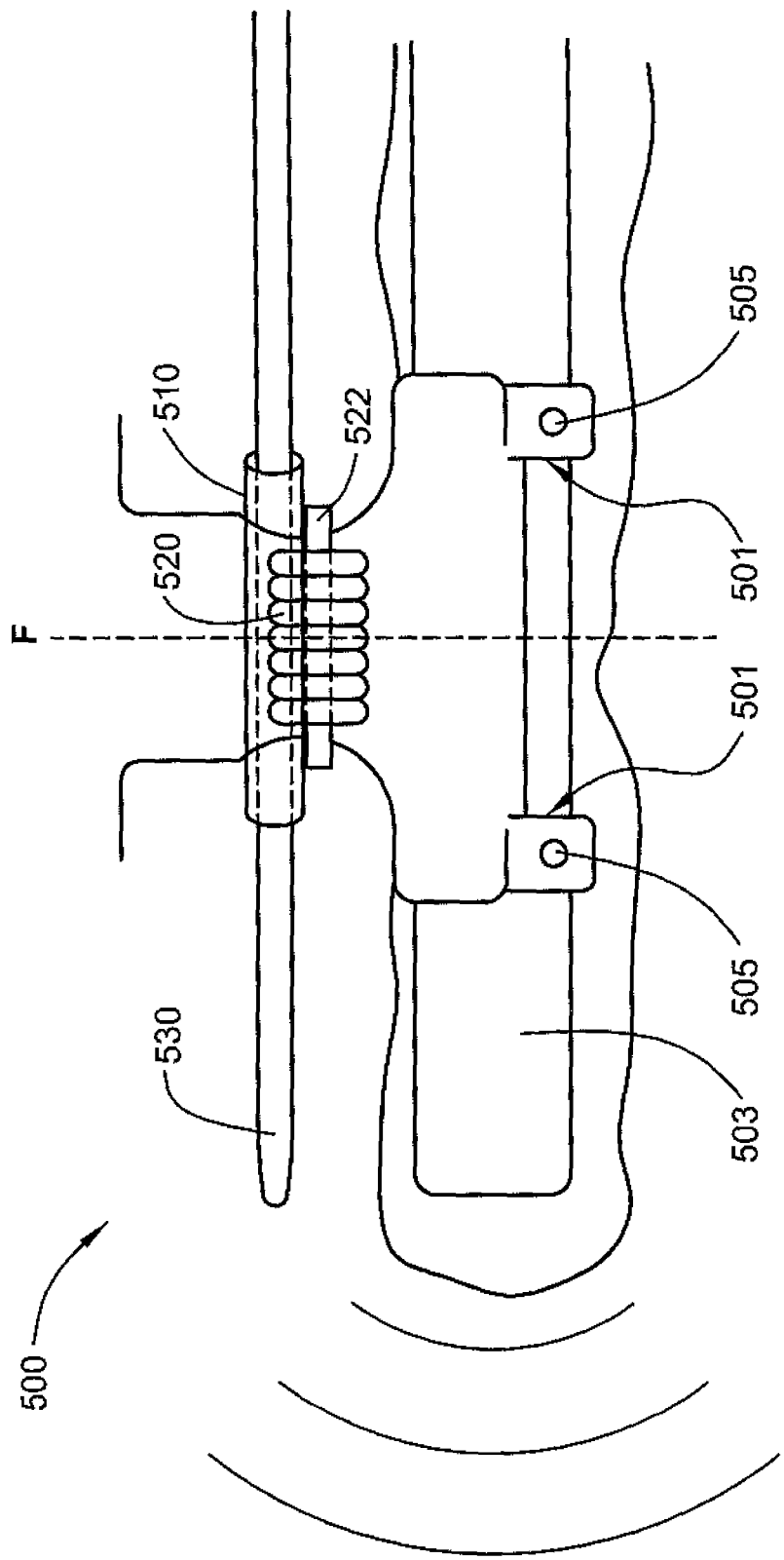
Figure 5B:
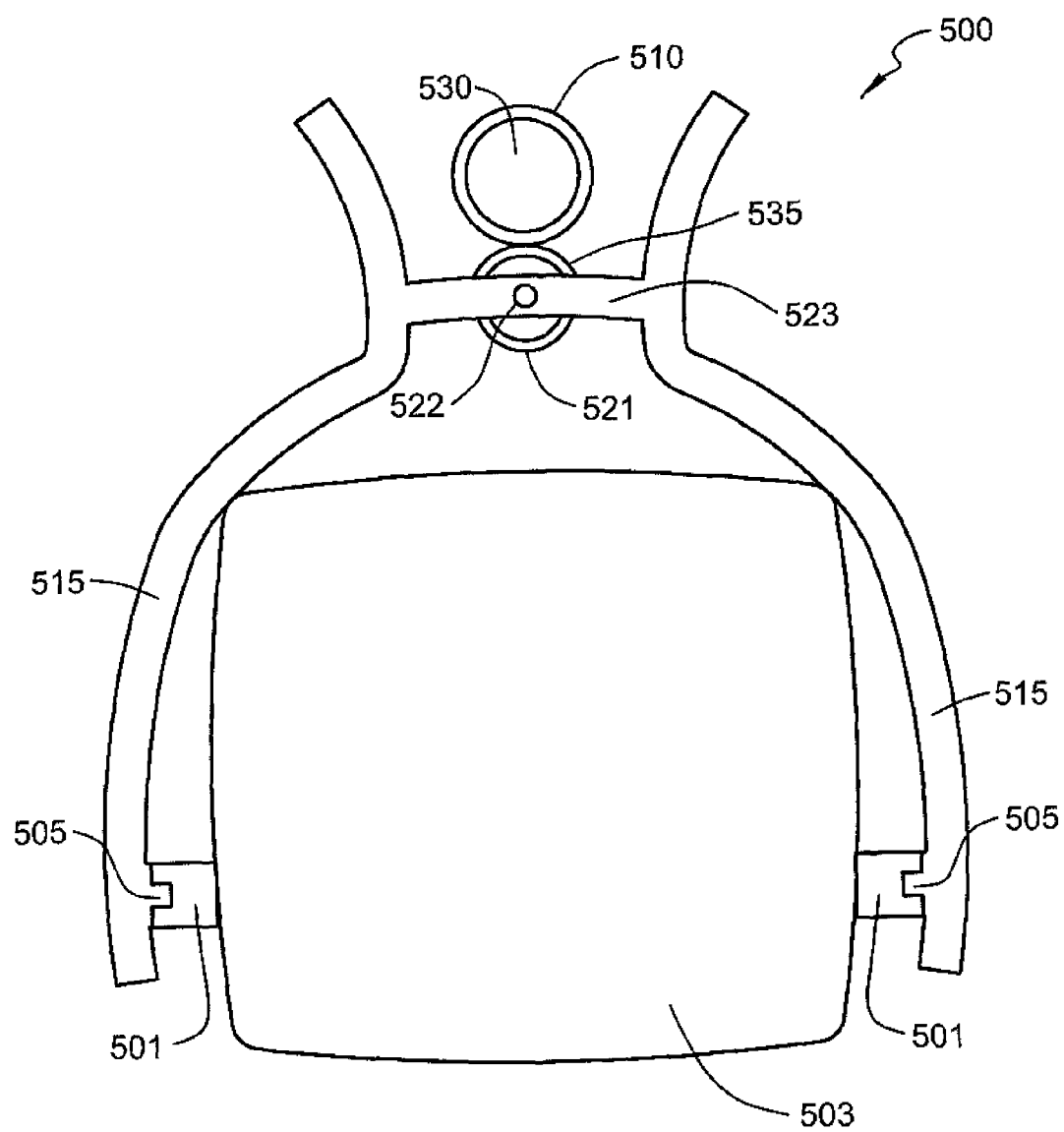

FIG. 5A is a schematic lateral view of an exemplary embodiment of the guiding-connector apparatus 500 of the present invention while FIG. 5B is a cross section view through line F of FIG. 5A of the present invention. The following description relates to FIGS. 5A and 5B in which guiding-connector apparatus 500 connects to holding recesses 501 pre installed on ultrasound probe 503 and are especially designed to fit holding pins 505 of guiding-connector apparatus 500. Typically a surgeon or a nurse will connect apparatus 500 to ultrasound probe 503 prior to the operation. Apparatus 500 comprises catheter holding member 510, fixation arms 515 and connector part 520. Catheter holding member 510 is attached to connector part 520 with attaching element 535 such as prefabricated plastic arm. Holding member 510 is preferably hollow having an aperture through which catheter 530 passes snugly. Fixation arms 515 are preferably V shaped plates interconnected in their middle part via connector part 520. Connector part 520 is a spring 521 and rod 522 connected to fixation arms via special attachments 523. Fixation arms 515 can be moved in relation to one another. When fixation arms are attached to ultrasound probe 503, specific pins 505 fit into recesses 501. In this exemplary embodiment, guiding connector apparatus 500 is held onto ultrasound probe 503 via tensile force of spring 521 as well as via attaching pin 505 to recesses 501.

Figure 6:
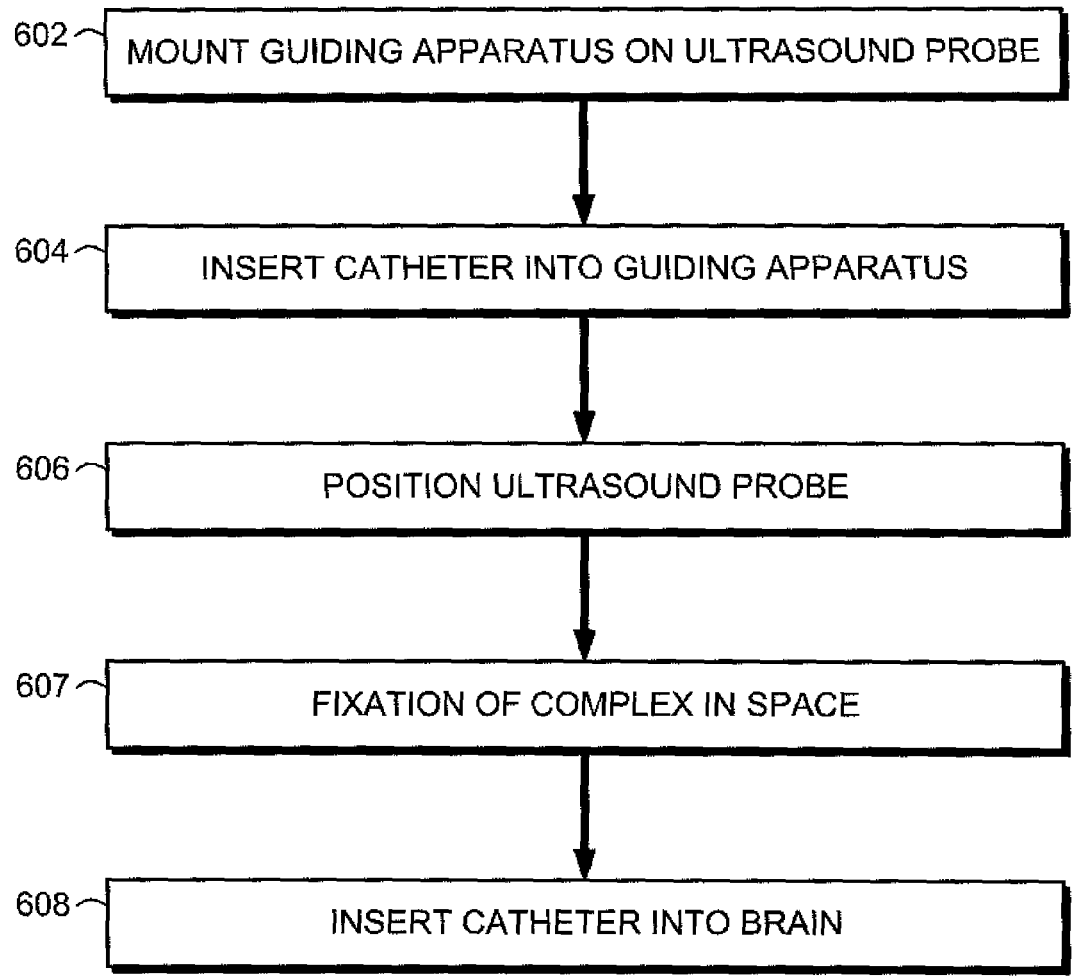
FIG. 6 is a flowchart of a method for inserting a shunt or catheter into a brain chamber, in accordance with exemplary embodiments of the subject matter.

FIG. 6 shows a flowchart 600, describing a method of using ultrasound and a guiding-connector apparatus to accurately insert a catheter or shunt into the brain, in accordance with an embodiment of the present invention and in accordance with FIGS. 2 and 3. In a specific embodiment of the present invention, the body organ is the brain or brain structure. In step 602, the guiding-connector apparatus 300 of FIG. 3 is mounted onto an ultrasound probe 320 of FIG. 3. In step 604 catheter 310 of FIG. 3 is inserted into catheter guiding member 304 of guiding-connector apparatus 300 of FIG. 3. In step 606 the complex (such as 230 of FIG. 2) is positioned in an appropriate trajectory (such as 214 of FIG. 2) to acquire target (such as 212 of FIG. 2) via ultrasound images of the desired body organ (such as 203 of FIG. 2). Calculations for best trajectory (such as 214 of FIG. 2) to acquire target 212 (such as 212 of FIG. 2) can be performed by ultrasound machine software (not shown here) such that alternative better trajectories can be presented to the operator (not shown) of complex (such as 230 of FIG. 2). In step 607, complex (such as 230 of FIG. 2) is fixated in space via fixating arm (not shown) such that when complex (such as 230 of FIG. 2) will not move while inserting catheter (such as 205 of FIG. 2) to target (such as 212 of FIG. 2). Fixation arm (not shown) can be a multiunit device or a simple arm holding complex (such as 230 of FIG. 2) to operating bed, a nearby member or the US device used in the procedure. In step 608 the catheter (such as 205 of FIG. 2) is inserted through brain (such as 220 of FIG. 2) into the brain ventricle 203 both of FIG. 2 using as guidance a trajectory (such as 214 of FIG. 2) determined using the ultrasound imaging probe (such as 209 also of FIG. 2). Alternatively, the catheter (such as 205 of FIG. 2) or Stillet (such as 325 of FIG. 3) may be inserted into the brain (such as 220 of FIG. 2) using as guidance an image generated by the data produced from the ultrasound probe (such as 209 of FIG. 2). The operator (not shown) may use the image to manually guide the catheter (such as 205 of FIG. 2) into target (such as 212 of FIG. 2).

Figure 7:
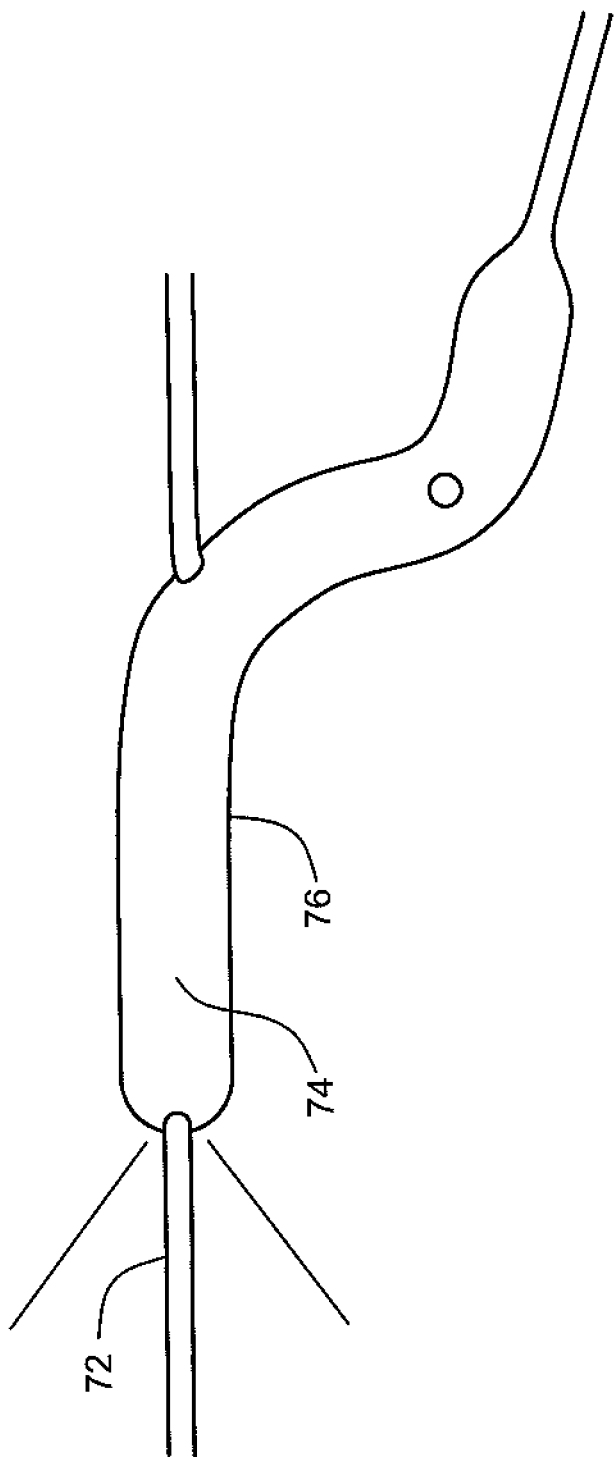
FIG. 7 shows a kit combining both imaging probe and a guiding catheter apparatus, in accordance with exemplary embodiments of the subject matter; and, FIG. 8 shows another exemplary embodiment of the disclosed apparatus.

FIG. 7 discloses a kit, combining both imaging probe 74 and catheter guiding apparatus 72. In this embodiment, the guiding apparatus is located within imaging probe assembly 76. Thus, the kit is less likely to be damaged since the structure requires no join between the probe and the guiding apparatus. Further, the kit provides more accurate functionality than a kit in which the guiding apparatus and the probe are attached with a guiding-connector. The improvement in accuracy is provided since the join used in the guiding-connector may be harmed and the angle between the main axis of the probe and the guiding apparatus is constant and unlikely to be modified. In addition, the kit is not time consuming in the sense of assembling the kit before surgery and disassembling the kit after use. Further, the specific structure provides the device with the same elements and with less surface area.

A major technical effect is provided in the disclosed subject matter by reaching better functionality with fewer elements. Further, it is more convenient for the user of the disclosed apparatus to use a kit in which the guiding catheter is mounted within the probe, since there is no offset between the probe and the catheter and guidance of the catheter is more intuitive and requires less consideration on the catheter apparatus.

In another exemplary embodiment of the disclosed apparatus, the apparatus further comprises a Doppler ultrasound transducer and a signal processing circuit, for ultrasonically sensing signals representative of blood flow within a patient. The signal processing unit may be mounted on a distal portion the guiding catheter, Turning now to FIG. 8 where yet another exemplary embodiment of the disclosed apparatus is described. The process of detecting brain ventricle in this embodiment is performed by using a Biosensor for beta transferrin. Beta transferrin is known to be CSF specific protein. In FIG. 8, a ventricular catheter apparatus 800 is shown. FIG. 8A illustrates the whole apparatus where external elements are visualized. FIGS. 8B and 8C each show both outer surface elements, depicted on the X side of the illustration. These include catheter 802, stylet 804, apertures 807 and stylet tip 806. Inner elements located beneath the surface, are depicted in the Y side of the illustration. These include biosensor 810, electrical connecting means 812, and indicator unit 814. Showing the device in such a manner allow the viewer to see the external and internal elements of the invention side by side.

The apparatus of the present invention described in FIG. 8 comprises a ventricular catheter apparatus 800, further comprising, catheter 802, stylet 804 and a bio-sensing module. In accordance with some exemplary embodiments of the subject matter, the bio sensing module comprises a biosensor 810, electrical connecting means 812 and indicator unit 814. The bio sensor module is functional in identifying and indicating the presence of a compound or material such as beta transferring. Other materials or compounds detected by the bio-sensor module when inserting a trocar or stylet into a body cavity or a tissue may be used by a person skilled in the art within the scope of this subject matter. The bio-sensing module detects and displays the presence of beta-transferrin or other predefined molecules in the body cavity or tissue. This embodiment comprises a ventricular catheter 802, Stylet 804, stylet tip 806, stylet tip apertures 807, stylet indicator 808, biosensor 810, electrical connecting means 812, indicator unit such as LED's 814.

Stylet 804 is continuous with stylet tip 806 whereas they form one unit used for penetrating a brain tissue by virtue of stylet rigid material strength and via force delivered to it by surgeon hand. Stylet 804 can be fabricated from metal or strong polymer materials. Surgeon (not shown) inserts ventricular catheter apparatus 800 through brain tissue (not shown) to roughly calculated brain ventricle location (not shown). It could be realized by a person skilled in the art that a use of a bio-sensor at one end of a stylet and catheter assembly may be used to detect and display the presence of material other than beta-transferrin. The biosensor 810, specific for beta transferrin molecule is situated preferably in the stylet tip 806. Biosensor 810 communicates with environment outside stylet tip 806 via aperture 807. It should be clear to the person skilled in the art that the word opening, port or aperture will hereon be used interchangeably. At least one aperture 807 is fabricated in stylet tip 806. Multiple ports 807 of different size and shape may be fitted with stylet tip 806. Ports 807 are larger than beta transferrin molecule but are preferably situated as to limit entry of large parts of tissue. This can be done by providing the port with small shield in their forward section (not shown). Inside stylet tip 806 is biosensor 810. Biosensor 810 is firmly attached to inside cavity formed in stylet 806. This cavity extend from stylet tip 806 to stylet 804 such that bio sensing module 810,812,814 can be accommodated and fastened with means known in the art. When beta transferrin binds to biosensing elements in biosensor 810, biosensor 810 is activated. Biosensor 810 can be fitted with ELISA (Enzyme Linked Imunosorbent Assay) type detection kit or with other kits for detecting bio-transferrin. Biosensor 810 preferably operates via electrical charge modulation, where binding with bio-transferrin changes charge capacity on the biosensor 810 leading to indication sent along electrical connecting means 812, either wired or wireless. This indication is used to activate indicator unit 814 such as LEDs or other visual or audio or tactual indicators. Data related to the detection of the predefined material may be sent to a remote location, and preferably displayed on a monitor on a remote location. Activation of indicator unit 814 indicate to the operating surgeon (not shown) that stylet tip 806 is in contact with beta-transferrin, thus within the brain ventricles CSF fluid (not shown). It should be noted that in accordance with some exemplary embodiments of the subject matter, the biosensor 810 is at least partially located outside the stylet 804. The bio-sensing module may further comprise a transmitter (not shown) for transmitting data related to the detection of the predefined material by the biosensor 810 or to the indication of such material. The data may be transmitted via RF communication, via the internet, or any other protocol or communicating device known to the person skilled in the art.

In accordance with another embodiment, the biosensor 810 is located on the external surface of the stylet. In such embodiment, as well as in other embodiments, the detection of the predefined material generates a signal, preferably a wirelessly transmitted signal, to be sent to a remote location.

It should be clear to the person skilled in the art that the use of a biosensor at the end of a stylet and catheter apparatus can be used for the detection of other material in human tissue during the insertion of a stylet and catheter assembly in order to identify specific environment or molecules.

It will be obvious to those skilled in the art that the guiding connector apparatus herein, while described in conjunction with brain surgery techniques, may also be used in other surgical environments where an accurate catheter insertion desired.

The present invention has been described using non-limiting detailed descriptions of embodiments thereof that are provided by way of example and are not intended to limit the scope of the invention. It should be understood that features described with respect to one embodiment may be used with other embodiments and that not all embodiments of the invention have all of the features shown in a particular figure or described with respect to one of the embodiments. It is noted that some of the above described embodiments may describe the best mode contemplated by the inventors and therefore include structure, acts or details of structures and acts that may not be essential to the invention and which are described as examples.

While the above description has focused on an apparatus, it is meant to also encompass methods for carrying out the invention.

When used herein, the terms "comprise", "include", "have" and their conjugates mean "including but not limited to".

The invention claimed is:

1. An ultrasound probe adapted for guiding the placement of a catheter, comprising:
   an ultrasound imaging probe;
   a catheter guiding apparatus;
   a plurality of catheter holding members for holding the catheter guiding apparatus;
   a plate having fastening elements connected thereto for fastening the ultrasound imaging probe to the ultrasound probe;
   wherein said plate further affixes said plurality of catheter holding members;
   wherein the ultrasound probe and the catheter guiding apparatus are positioned on different sides of the plate.

2. The ultrasound probe according to claim 1, further comprising a Doppler ultrasound transducer and a signal processing circuit, for sensing signals representative of blood flow within a patient.

3. The ultrasound probe according to claim 1, wherein the catheter guiding apparatus comprises a tubular unit having an opening and a curved cross-sectional area dimensioned to receive a catheter of a predetermined diameter.

4. A method of accurately inserting a catheter or trocar into a patient's brain, the method comprising:
   mounting a catheter guiding apparatus on an ultrasound probe to form an ultrasound probe-catheter guiding complex, a plurality of catheter holding members for holding the catheter guiding apparatus;
   wherein the catheter guiding apparatus comprises a plate having fastening elements connected thereto for fastening the ultrasound imaging probe to the ultrasound probe;
   wherein said plate further affixes said plurality of catheter holding members;
   wherein the ultrasound probe and the catheter guiding apparatus are positioned on different sides of the plate;
      inserting a catheter or a trocar through the mounted catheter guiding apparatus;
      determining a trajectory using the ultrasound imaging probe;
      fixing said ultrasound probe-catheter guiding complex in space; and,
      inserting the catheter or a trocar through the mounted catheter guiding apparatus into the patient's brain through an opening in the patient's skull, using the determined trajectory.

\* \* \* \* \*